US009714209B2

United States Patent
Kim et al.

(10) Patent No.: US 9,714,209 B2
(45) Date of Patent: Jul. 25, 2017

(54) ESTOLIDE COMPOUND AND METHOD FOR PREPARING THE SAME

(71) Applicants: SK Innovation Co., Ltd., Seoul (KR); SK Lubricants Co., Ltd., Seoul (KR)

(72) Inventors: Yong Woo Kim, Daejeon (KR); Hee Jung Jeon, Daejeon (KR); Wan Seop Kwon, Daejeon (KR); Hak Mook Kim, Daejeon (KR); Jin Hee Ok, Daejeon (KR)

(73) Assignees: SK Innovation Co., Ltd., Seoul (KR); SK Lubricants Co., Ltd., Seoul (KR)

( * ) Notice: Subject to any disclaimer, the term of this patent is extended or adjusted under 35 U.S.C. 154(b) by 112 days.

(21) Appl. No.: 14/793,010

(22) Filed: Jul. 7, 2015

(65) Prior Publication Data

US 2016/0009630 A1    Jan. 14, 2016

(30) Foreign Application Priority Data

Jul. 8, 2014 (KR) .................. 10-2014-0084969

(51) Int. Cl.
*C07C 59/00* (2006.01)
*C07C 67/04* (2006.01)
(Continued)

(52) U.S. Cl.
CPC ............ *C07C 67/04* (2013.01); *C07C 1/2078* (2013.01); *C07C 1/24* (2013.01); *C07C 29/149* (2013.01); *C07C 51/36* (2013.01); *C07C 51/44* (2013.01); *C07C 67/08* (2013.01); *C07C 69/67* (2013.01); *C10M 105/42* (2013.01); *C10M 107/30* (2013.01); *C07C 2531/24* (2013.01);
(Continued)

(58) Field of Classification Search
CPC ... C07C 67/104; C07C 1/2018; C10M 105/42
USPC ............................................. 554/122
See application file for complete search history.

(56) References Cited

U.S. PATENT DOCUMENTS 8,450,256 B2    5/2013    Bredsguard
2012/0172609 A1    7/2012    Bredsguard
(Continued)

FOREIGN PATENT DOCUMENTS

FR            885865        9/1943

OTHER PUBLICATIONS

TRC110 Product Specification, Nov. 2012, Twin Rivers Technologies, http://www.twinriverstechnologies.com/products/whole_cut_acids.html.*

(Continued)

*Primary Examiner* — Deborah D Carr
(74) *Attorney, Agent, or Firm* — The Webb Law Firm

(57) ABSTRACT

A method for preparing an estolide compound and an estolide compound prepared thereby are disclosed. The method for preparing an estolide compound includes: converting biomass fat into a fatty acid; separating the fatty acid into a $C_{16}$ saturated fatty acid and a $C_{18}$ unsaturated fatty acid; preparing a linear internal olefin (LIO); increasing an amount of oleic acid through partial hydrogenation of the $C_{18}$ unsaturated fatty acid; synthesizing an estolide polymer through cross metathesis of the oleic acid; capping the $C_{16}$ saturated fatty acid onto the estolide polymer; and reacting the estolide polymer with the linear internal olefin.

14 Claims, 7 Drawing Sheets

(51) Int. Cl.
*C10M 105/42* (2006.01)
*C07C 29/149* (2006.01)
*C07C 67/08* (2006.01)
*C07C 69/67* (2006.01)
*C07C 51/36* (2006.01)
*C07C 1/207* (2006.01)
*C07C 1/24* (2006.01)
*C07C 51/44* (2006.01)
*C10M 107/30* (2006.01)

(52) U.S. Cl.
CPC ........... *C10M 2207/301* (2013.01); *C10M 2209/1105* (2013.01); *C10N 2220/022* (2013.01); *C10N 2220/023* (2013.01); *C10N 2230/02* (2013.01); *C10N 2270/00* (2013.01)

(56) References Cited

U.S. PATENT DOCUMENTS

2012/0322897 A1* 12/2012 Bredsguard .......... C10M 169/04
514/785
2014/0012023 A1 1/2014 Thompson et al.

OTHER PUBLICATIONS

Isbell, Chemistry and Physical Properties of Estolides, United States Department of Agriculture, Agriculture Research Service, National Center for Agricultural Utilization Research, 2011, p. 8-20.
Cermak, S.C. et al. "Physical Properties of Saturated Estolides and their 2-ethylhexyl esters", Industrial Crops and Products, 2002, pp. 119-127, vol. 16.

* cited by examiner

ESTOLIDE COMPOUND AND METHOD FOR PREPARING THE SAME

CROSS-REFERENCE TO RELATED APPLICATION

This application claims priority to and the benefit of Korean Patent Application No. 10-2014-0084969, filed on Jul. 8, 2014 in the Korean Intellectual Property Office, the entire disclosure of which is incorporated herein by reference.

FIELD OF THE INVENTION

The present invention relates to an estolide compound and a method for preparing the same, and more particularly, to an estolide compound, which does not include an unsaturated bond and exhibits excellent low-temperature stability and oxidative stability, and a method for preparing the same.

DESCRIPTION OF THE RELATED ART

To prepare an environmentally friendly lubricating oil which exhibits high biodegradability and is free from toxic substances such as S, N, aromatics and heavy metals, a technique for preparing a biomass-derived lubricating oil is proposed.

Recently, estolides are a focus of attention as a biomass-derived environmentally friendly lubricating oil. Materials in which an unsaturated double bond in a hydrocarbon is crosslinked with a carboxyl group are collectively referred to as estolides. Estolides can be naturally derived from castor bean or lesquerella derived vegetable oils. It was known in the art by Penoyer et al. in 1954 that estolides could be prepared by simple synthesis, whereby a possibility of producing estolides as a novel product was suggested.

Although it was recognized from the beginning that there was a possibility of applying estolides as a lubricating oil (Group V, ester base oil) due to structural properties thereof, since triglyceride-derived estolides, which were proposed in the initial stage, did not secure sufficient oxidative stability despite excellent pour point thereof, triglyceride-derived estolides were unsuitable for use as a lubricating oil.

In *Chemistry and physical properties of estolide* (Isbell, 2011), a 4-step process composed of (1) de-esterification, (2) estolide synthesis, (3) esterification and (4) hydrogenation is disclosed as a process for preparing an estolide. De-esterification is a process of converting triglycerides, which make up the majority of biomass fat, into a fatty acid; estolide synthesis is a process of converting an unsaturated fatty acid into an estolide; esterification is a process of stabilizing the estolide through change into an ester by reacting a carboxyl group present in the estolide with alcohols; and hydrogenation is a process of improving oxidative stability of the estolide by removing an unsaturated double bond present in the estolide.

The prepared estolide exhibits properties of a high quality lubricating base oil that exhibits higher viscosity index, oxidative stability and thermal stability than typical petroleum-based Group I, Group II and Group III base oils, and has a great merit as a lubricating oil in that the estolide can be made into a high-viscosity lubricating base oil based on 100 vis.

However, existing methods for preparing an estolide have fundamental problems as follows.

The first problem is dependency on oleic acid. In initial stages of estolide research, research into preparing an estolide from a triglyceride itself and then using the prepared estolide as a lubricating base oil was carried out. However, since the estolide exhibited poor low-temperature stability when the triglyceride was directly used, the estolide was unsuitable for use as a lubricating base oil. On the other hand, oleic acid was selectively used as a raw material for preparing the estolide, whereby the problem of low-temperature stability of the estolide was significantly reduced while improving other properties of the estolide. However, it could be seen that dependency on oleic acid was significantly increased in the preparation of the estolide. Supply of biomass-derived oleic acid is inherently limited. For example, an amount of oleic acid contained in crude palm oil (CPO) is no more than about 52% by weight (wt %). Therefore, only the content of oleic acid in the biomass fat is used in the preparation of the estolide, and the amount of oleic acid is no more than about 50% in the biomass fat. In addition, there is a problem in that use of the remaining fatty acids excluding oleic acid should be considered.

The second problem is that alcohol is necessary for esterification. Since a fatty acid group is present in the estolide due to estolide reaction and thus can cause various problems such as material instability, corrosiveness, and the like, the estolide must be made into another stable form. In most cases, the estolide is made into an ester form which exhibits high stability and can provide volume gain. Existing estolides are also stabilized in the form of an ester through reaction of an acid group with alcohol. In other words, for reaction stability, it can also be understood that alcohol is necessary. Since alcohol is not created during reaction, there is a problem in that alcohol must be introduced from the outside.

The third problem is that hydrofinishing is necessary. In a typical process for preparing an estolide, hydrofinishing is performed to remove an unsaturated double bond derived from biomass fat. Since the unsaturated double bond can cause deterioration in oxidative stability, it is necessary to remove the unsaturated double bond through hydrogenation. In an existing reaction for preparing estolide, the unsaturated double bond in an estolide structure is also removed by hydrofinishing. However, there are problems in that hydrofinishing is performed by hydrogenation under conditions of high temperature and high pressure and is not economically feasible due to high price of hydrogen.

The fourth problem is that the unsaturated double bond remains in the existing estolide even though the reaction for removing the unsaturated double bond is applied through hydrogenation. Fundamentally, since a lubricating oil can suffer from side reaction such as discoloration due to bonding of the unsaturated double bond to oxygen in air, increased corrosiveness due to increased hygroscopicity, and the like when the unsaturated double bond is present in the molecular structure of the lubricating oil, the remaining unsaturated double bond is generally completely removed through hydrogenation. However, since an ester bond of the estolide can be partially broken during reaction for completely removing the remaining unsaturated double bond, selective removal of the unsaturated double bond is performed under conditions that the ester bond is maintained. For this reason, the unsaturated double bond is not completely removed. Although the estolide has a low iodine value of less than 10, the unsaturated double bond can remain in the estolide.

The fifth problem is that an existing estolide has an ester group exhibiting low steric hindrance. Esterification has a merit in that structural stability unique to an ester and volume gain due to alcohol can be obtained. However, the ester group exhibits relatively higher stability than other functional groups, and cannot be thought absolutely stable. The ester group can be irreversibly converted into a fatty acid depending on reaction conditions, and, in this case, there can be a serious problem of engine corrosion. In fact, in the case of FAME which is in an ester form and is first generation biodiesel, or an ester base oil which is a Group V base oil, engine corrosion caused by a fatty acid created due to the broken ester group has been reported. To overcome these problems, other forms of diesel or anti-corrosion additives are used together.

SUMMARY OF THE INVENTION

It is one aspect of the present invention to provide an estolide compound exhibiting excellent low-temperature stability and oxidative stability.

It is another aspect of the present invention to provide an estolide compound free from an unsaturated bond.

It is a further aspect of the present invention to provide a method for preparing an estolide compound, which exhibits excellent economic feasibility by converting the remaining fatty acids excluding oleic acid out of biomass-derived fatty acids into a linear internal olefin (LIO).

It is yet another aspect of the present invention to provide a method for preparing an estolide compound, which can improve economic feasibility through minimization of dependency on oleic acid in the preparation of the estolide compound by increasing the content of oleic acid.

It is yet another aspect of the present invention to provide a method for preparing an estolide compound, which does not require use of alcohols.

It is yet another aspect of the present invention to provide a method for preparing an estolide compound, which does not require separate hydrofinishing.

One aspect of the present invention relates to a method for preparing an estolide compound, which includes: converting biomass fat into a fatty acid; separating the fatty acid into a $C_{16}$ saturated fatty acid and a $C_{18}$ unsaturated fatty acid; preparing a linear internal olefin (LIO); increasing an amount of oleic acid through partial hydrogenation of the $C_{18}$ unsaturated fatty acid; synthesizing an estolide polymer through cross metathesis of the oleic acid; capping the $C_{16}$ saturated fatty acid onto the estolide polymer; and reacting the estolide polymer with the linear internal olefin.

Another aspect of the present invention relates to an estolide compound represented by Formula 2:

DETAILED DESCRIPTION OF THE INVENTION

Method for Preparing Estolide Compound

Figure 1:
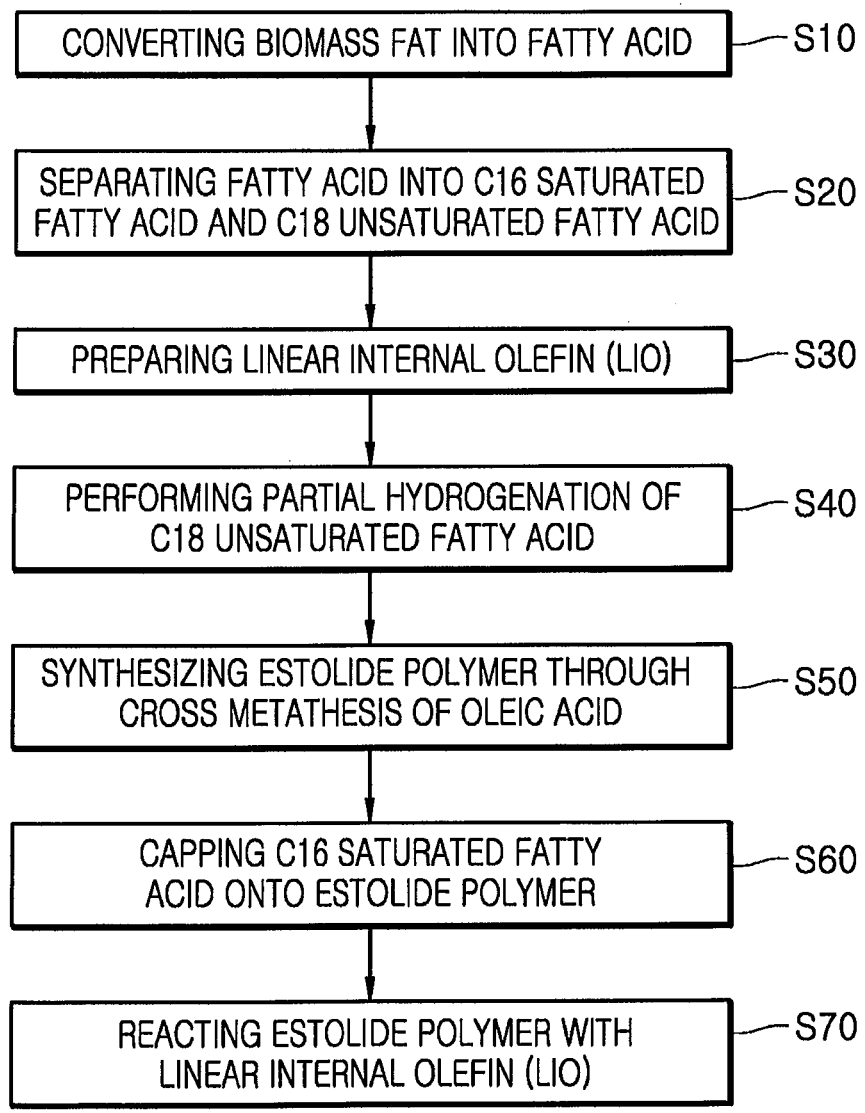
FIG. 1 is a flowchart showing stages of a method for preparing an estolide compound according to one embodiment of the present invention.

FIG. 1 is a flowchart showing stages of a method for preparing an estolide compound according to one embodiment of the present invention. Referring to FIG. 1, a method for preparing an estolide compound according to one embodiment includes: converting biomass fat into a fatty acid (S10); separating the fatty acid into a $C_{16}$ saturated fatty acid and a $C_{18}$ unsaturated fatty acid (S20); preparing a linear internal olefin (LIO) (S30); increasing an amount of oleic acid through partial hydrogenation of the $C_{18}$ unsaturated fatty acid (S40); synthesizing an estolide polymer through cross metathesis of the oleic acid (S50); capping the $C_{16}$ saturated fatty acid onto the estolide polymer (S60); and reacting the estolide polymer with the linear internal olefin (LIO) (S70).

Figure 2:
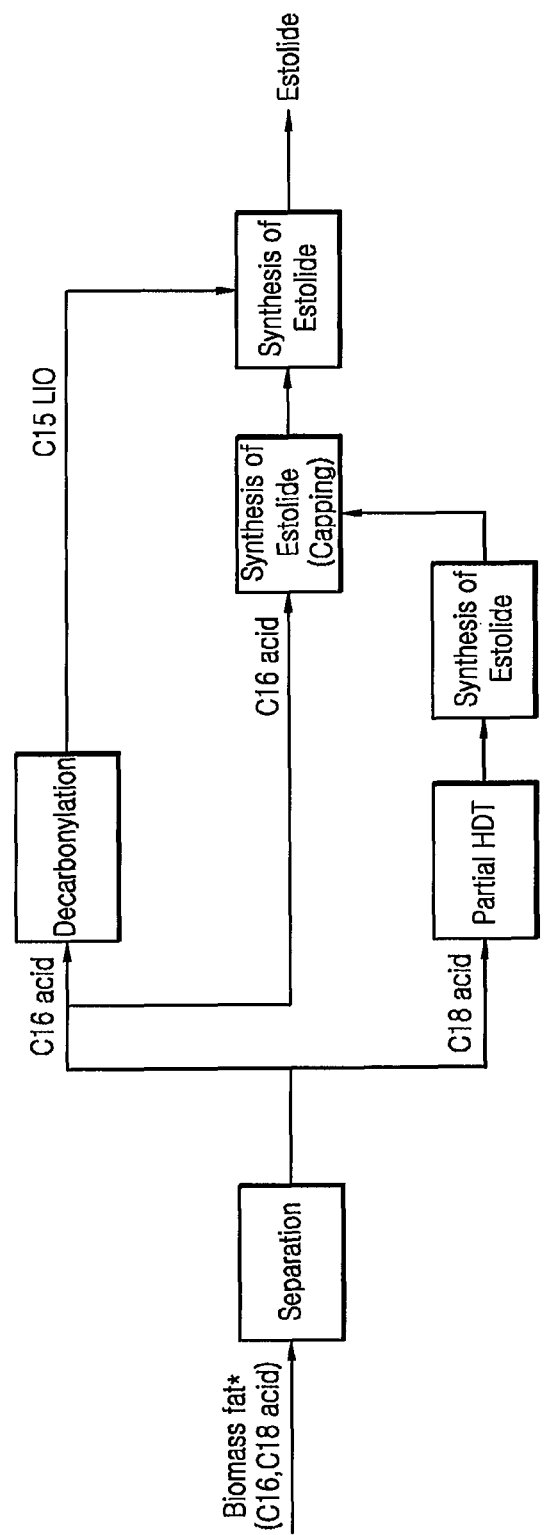
FIG. 2 is a process flowchart schematically showing a method for preparing an estolide compound according to one embodiment of the present invention.
Figure 3:
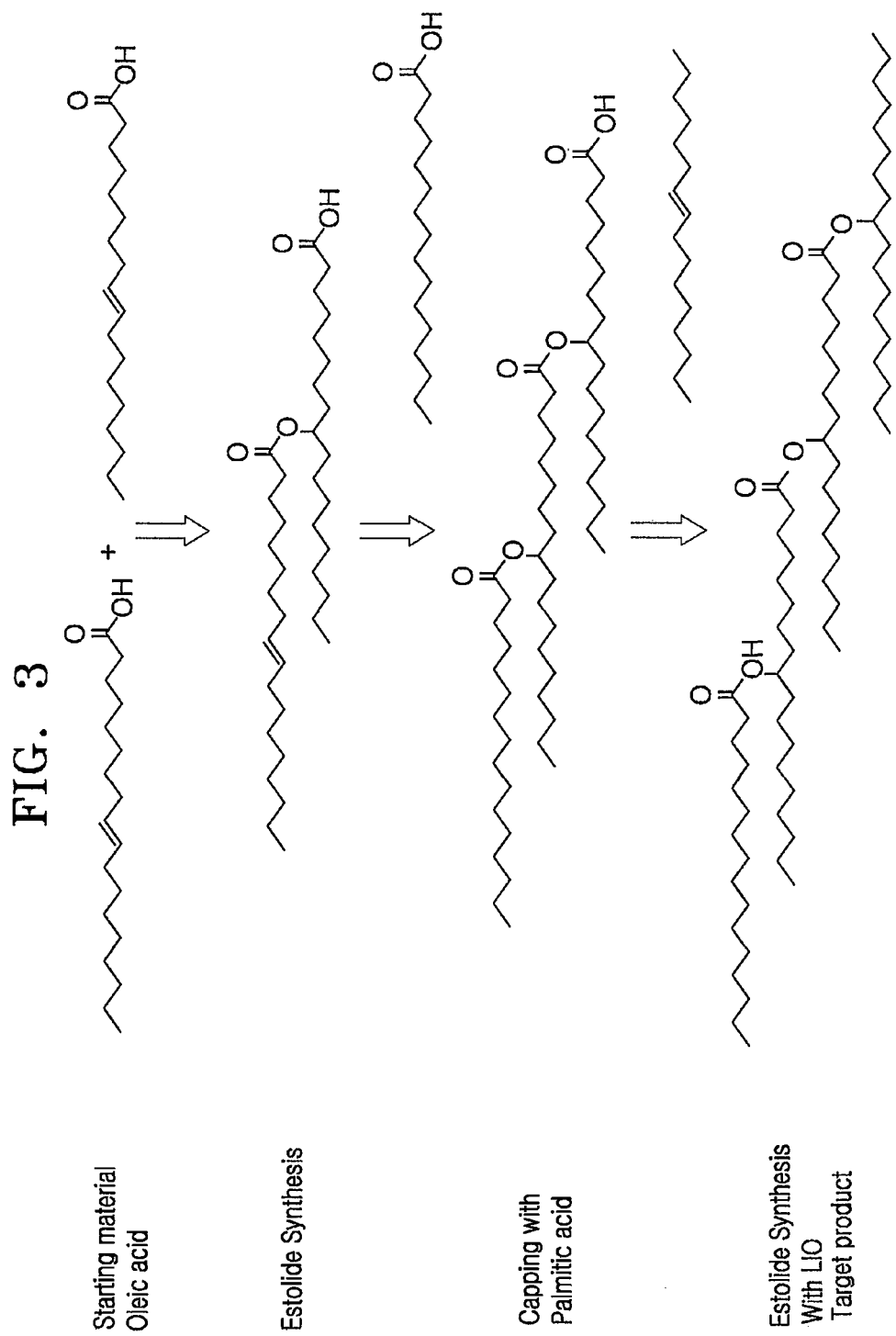
FIG. 3 shows a reaction mechanism of an estolide compound according to one embodiment of the present invention.

FIG. 2 is a process flowchart schematically showing a method for preparing an estolide compound according to one embodiment of the present invention, and FIG. 3 shows a reaction mechanism of an estolide compound according to one embodiment of the present invention. Hereinafter, each of the stages of the method will be described in detail with reference to FIGS. 2 and 3.

As generally known in the art, operation S10 of converting biomass fat into a fatty acid may be performed by extracting a triglyceride from the biomass using a strong

[Formula 2]

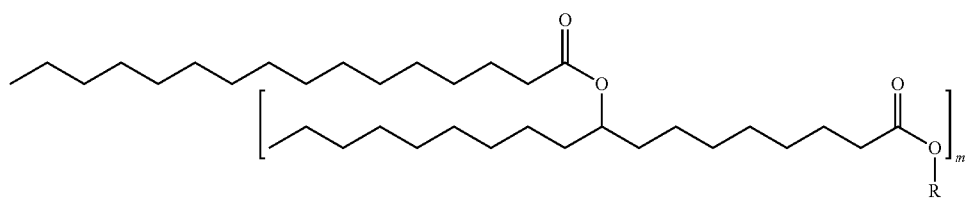

wherein m is an integer of 1 to 6 and R is a $C_{2n}$ or $C_{2n+1}$ alkyl group (n being an integer of 2 to 12).

A further aspect of the present invention relates to a lubricating oil including the estolide compound as set forth above.

acid, a strong base, high-temperature steam and the like, followed by converting the triglyceride into a fatty acid through hydrolysis of an ester bond of the triglyceride.

Since the fatty acid derived from the biomass fat includes various saturated fatty acids and unsaturated fatty acids, operation S20 of separating the fatty acid into a $C_{16}$ saturated fatty acid and a $C_{18}$ unsaturated fatty acid is performed. For example, fatty acids derived from crude palm oil may include myristic acid, palmitic acid, oleic acid, linoleic acid, linolenic acid, monoglycerides, and diglycerides. As such, since such various fatty acids have different boiling points, a desired fatty acid may be selectively extracted and separated through fractional distillation.

Therefore, the biomass-derived fatty acid may be separated and extracted into the $C_{16}$ saturated fatty acid (b.p. 300° C. to 355° C.) and the $C_{18}$ unsaturated fatty acid (b.p. 355° C. to 380° C.) through fractional distillation. The $C_{16}$ saturated fatty acid may be palmitic acid and the $C_{18}$ unsaturated fatty acid may include oleic acid, linoleic acid and linolenic acid.

Next, operation S30 of preparing a linear internal olefin (LIO) is, for example, a process of converting the biomass-derived fatty acid converted in operation S10 into the LIO. Esterification is performed by reacting the prepared LIO with a fatty acid group placed at a terminal of an estolide polymer described below, thereby providing stability to a chemical structure.

In a method for converting a fatty acid into an LIO according to one embodiment, the biomass-derived fatty acid may be converted into the LIO by deriving decarbonylation in the presence of a metal chelating agent in a batch reactor. For example, since most biomass-derived fatty acids are $C_{16}$ and $C_{18}$ fatty acids, the $C_{16}$ and $C_{18}$ fatty acids may be converted into $C_{15}$ and $C_{17}$ LIOs when subjected to decarbonylation. However, compositional properties are not limited thereto since the compositional properties can vary with origins of biomass.

The catalyst used in decarbonylation may be, for example, a transition metal chelating agent, without being limited thereto. The catalyst may be any catalyst without limitation so long as the catalyst can allow an olefin, that is, a double bond, to be created from a fatty acid.

The transition metal may be a transition metal belonging to Groups VIII to X of the periodic table, more specifically Pd, Rh, Ir, Cu, Fe or the like. In addition, a ligand used as a chelating agent may be representatively a phosphorus ligand, specifically a phosphine ligand. Particularly, the phosphine ligand may include triphenylphosphines, $C_4$ to $C_7$ paraffin diphenylphosphine, and the like. Here, the ligand may be present in an amount of about 1 mol to about 50 mol, specifically about 1 mol to about 20 mol, more specifically about 1 mol to about 10 mol based on 1 mol of the transition metal in the catalyst. Further, to increase reaction activity of decarbonylation or to control a position of a double bond in an olefin product, at least one of CO and a halogen may be introduced as a chelating agent into the catalyst. The halogen element is preferably chlorine (Cl).

Reaction Formula 1 shows a mechanism of decarbonylation performed in the presence of a transition metal chelating agent represented by Formula 1.

[Reaction Formula 1]

[Formula 1]

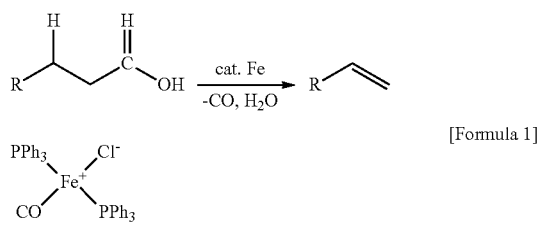

To continuously maintain decarbonylation by removing $H_2O$ created due to decarbonylation and driving polycondensation of the fatty acid, an acid anhydride may be included in the reaction system. Examples of the acid anhydride may include acetic anhydride, propionic anhydride, and the like. A molar ratio of the fatty acid to the acid anhydride ranges from about 1:2 to about 1:50, preferably from about 1:2 to about 1:20, more preferably from about 1:2 to about 1:10. In addition, the acid anhydride may be introduced into the reaction system in a CO or $N_2$ atmosphere.

Decarbonylation may be performed at a reaction temperature of about 120° C. to about 400° C., specifically about 150° C. to about 300° C., more specifically about 180° C. to about 250° C. and at a reaction pressure of about 50 bar or less, specifically about 30 bar or less, more specifically about 1 bar to about 20 bar in terms of CO.

Decarbonylation may be performed in a batch reactor or a continuous flow reactor.

A mixed fatty acid, which is a raw material of decarbonylation, may be derived from triglycerides or be a preexisting free fatty acid, and may include a certain level of unsaturated fatty acid containing a double bond. In addition, decarbonylation of the mixed fatty acid may be performed at a relatively lower reaction temperature than decarbonylation of only a saturated fatty acid.

In decarbonylation as set forth above, it should be noted that a position of a double bond of a created mixed olefin has a meaningful influence on properties of a final estolide compound.

Figure 4:
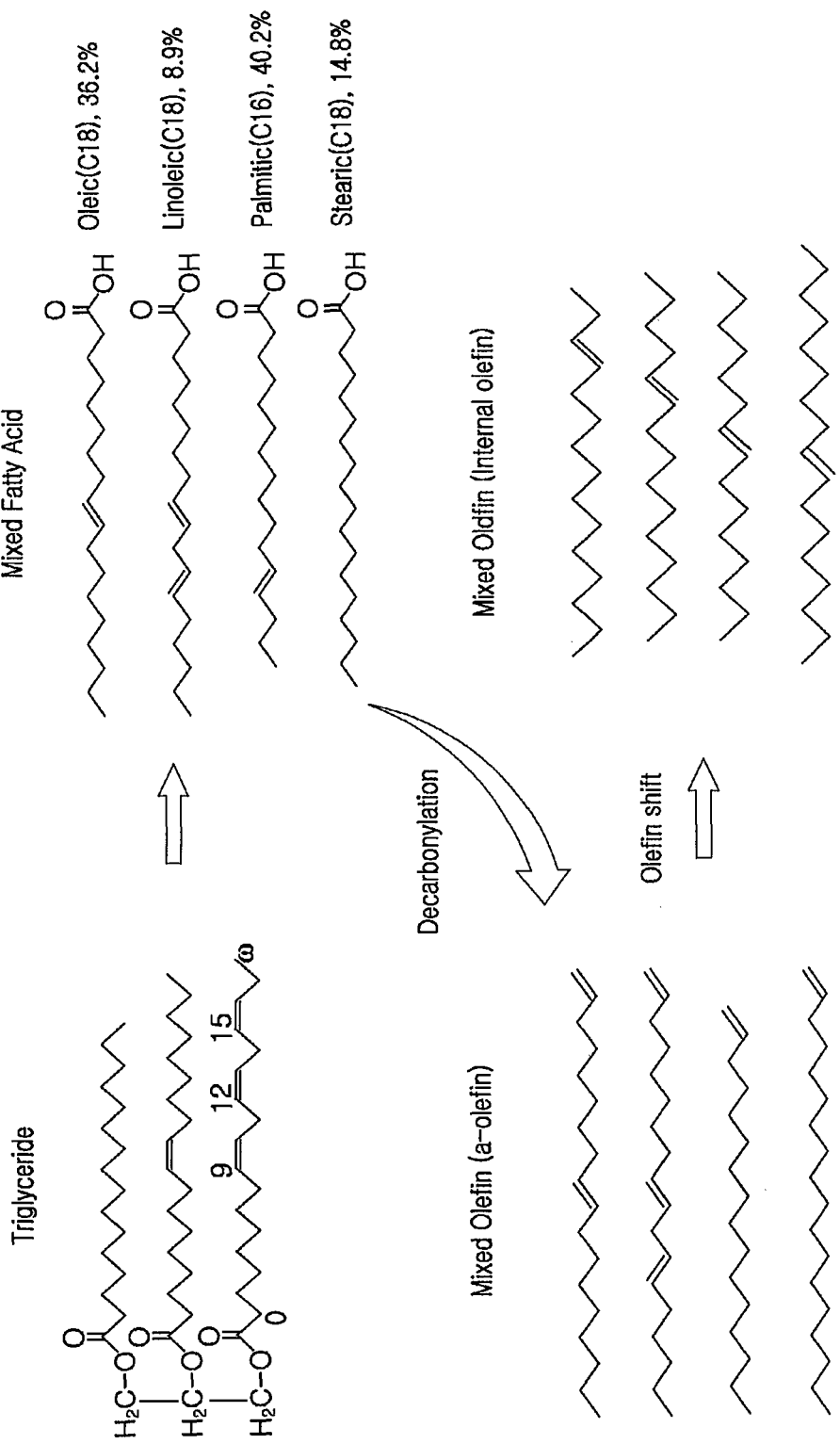
FIG. 4 schematically shows a reaction mechanism for synthesizing a linear internal olefin (LIO) from triglycerides.

FIG. 4 schematically shows a reaction mechanism for synthesizing a linear internal olefin (LIO) from triglycerides, and is a flowchart showing a reaction path for preparing the mixed olefin through decarbonylation of the mixed fatty acid converted from triglycerides. Referring to FIG. 4, as a result of decarbonylation of the mixed fatty acid derived from triglycerides, a double bond is formed at an alpha position of α-olefin which is a product in the reaction mechanism. Depending on reaction conditions, the double bond may be shifted to a center of a carbon chain and thus be converted into an internal olefin. In addition, a double bond present in the fatty acid before decarbonylation may also be shifted in some cases.

Selectivity for the α-olefin or the internal olefin may be controlled by controlling reaction temperature and reaction time upon decarbonylation. For example, if a low reaction temperature and a short reaction time are set for decarbonylation, selectivity for the α-olefin in a created olefin can be increased, and if a high reaction temperature and a long reaction time are set for decarbonylation, selectivity for the internal olefin can be increased.

Specifically, decarbonylation may be performed at less than about 250° C., more specifically less than about 240° C. For example, in the case of a fatty acid distillate such as PFAD, decarbonylation may be performed at about 180° C. to about 250° C. Here, the reaction time may range from about 1 minute to about 600 minutes, specifically from about 1 minute to about 180 minutes, more specifically from about 1 minute to about 60 minutes. Specifically, when the reaction temperature of decarbonylation is about 240° C., the internal olefin can be formed by shift of the double bond of the alpha position in the created olefin. The α-olefin in the mixed olefin may be optionally present in an amount of about 80 mol % or less, specifically about 70 mol % or less, without being limited thereto. In addition, a desired ratio of the α-olefin to the internal olefin can be achieved by appropriately adjusting reaction conditions of decarbonylation.

A method for converting a fatty acid into an LIO according to another embodiment includes converting $C_{16}$ and $C_{18}$ fatty acids into $C_{16}$ and $C_{18}$ LIOs using partial hydrogenation and dehydration. That is, the fatty acid is converted into a fatty alcohol through partial hydrogenation, and then converted into the LIO through dehydration.

In one embodiment, various catalysts may be used in reaction for converting a fatty acid into an alcohol through partial hydrogenation. For example, the catalyst may be a transition metal of Groups VIII to X in the periodic table, specifically Pd, Rh, Ir, Cu, Fe or the like.

Partial hydrogenation may be performed at a temperature of about 120° C. to about 500° C., specifically about 150° C. to about 350° C., more specifically about 200° C. to about 300° C. and at a pressure of about 50 bar or less, specifically about 30 bar or less, more specifically about 1 bar to about 70 bar in terms of $H_2$.

Partial hydrogenation may be performed in a batch reactor or a continuous flow reactor, and it is desirable that partial hydrogenation be performed in a fixed bed reactor for large-scale commercial application. In addition, partial hydrogenation may be performed at a weight hourly space velocity (WHSV) of about 0.05 $h^{-1}$ to about 10 $h^{-1}$, specifically about 0.1 $h^{-1}$ to about 3 $h^{-1}$, more specifically about 0.5 $h^{-1}$ to about 2 $h^{-1}$ and in a gas oil ratio (GOR) of about 50 to about 5,000, specifically about 300 to about 2,500, more specifically about 500 to about 1,500.

Reaction for converting a fatty acid into alcohol includes: converting a fatty acid into an ester; and creating alcohol from the ester through hydrogenation, that is, partial hydrogenation. Of course, although these two steps are sequentially performed, it is possible to find operation conditions under which yield of the ester corresponding to an intermediate product is low due to an extremely high reaction rate. For this reason, in the reaction for converting a fatty acid into alcohol, alcohol may be additionally introduced to easily convert the fatty acid into the ester corresponding to the intermediate product. The introduced alcohol may be methanol which is a lower alcohol.

The reaction in which the ester is created through esterification by adding alcohol to the acid and then converted into alcohol may be represented by Reaction Formula 2.

[Reaction Formula 2]

RCOOH+R'OH→RCOOR'+H$_2$O  (I)

RCOOR'+2H$_2$→RCH$_2$OH+R'OH  (II)

As shown in Reaction Formula 2, the alcohol introduced to convert the fatty acid into alcohol can be recovered and reused since there is no change in a structure of the introduced alcohol even after reaction.

In addition, without addition of the alcohol, the reaction may be derived only by the fatty acid as in Reaction Formula 3.

[Reaction Formula 3]

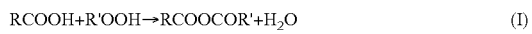
RCOOH+R'OOH→RCOOCOR'+H$_2$O  (I)

RCOOCOR'+2H$_2$→RCOOH+R'CH$_2$OH  (II)

RCOOH+R'CH$_2$OH→RCOOCH$_2$R'+H$_2$O  (III)

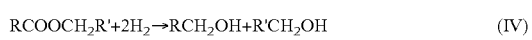
RCOOCH$_2$R'+2H$_2$→RCH$_2$OH+R'CH$_2$OH  (IV)

As shown in Reaction Formula 3, even though the alcohol is not additionally used, the fatty acid may be converted into a structure of a polycondensate (acid anhydride) and then converted into alcohol via an ester form.

The converted fatty alcohol may be converted into an olefin by dehydration in the presence of a metal oxide catalyst in a fixed bed reactor.

In one embodiment, the metal oxide catalyst used in dehydration may be any material so long as the material has a weak acid site. For example, shift control of a double bond of the olefin can be achieved by increasing the reaction temperature in use of a weak acid site-containing material such as zirconia and by decreasing the reaction temperature in use of a strong acid site-containing material such as zeolite. Examples of the metal oxide catalyst may include alumina, silica-alumina, zirconia, titania, iron oxide, vanadium oxide, zeolite, alumina-supported mesoporous silica, and the like.

Dehydration may be performed at 250° C. to 500° C., and a position of the double bond in the olefin may be moved during reaction depending on the degree of dehydration.

Due to these characteristics, by controlling reaction conditions, the created olefin may be prepared as a linear internal olefin (LIO) rather than a linear alpha olefin (LAO), and double bond position distribution in the LIO can also be controlled.

Dehydration may be performed, for example, in a fixed bed reactor. Examples of an inert gas injected into the fixed bed reactor may include nitrogen (N2), argon (Ar), helium (He), and the like. In addition, the inert gas may be injected at a flow rate of 10 sccm to 1000 sccm, specifically 30 sccm to 200 sccm.

Dehydration is performed at a weight hourly space velocity (WHSV) of the fixed bed reactor of 0.01 $h^{-1}$ to 50 $h^{-1}$, preferably 0.1 to 3 $h^{-1}$.

Although only an olefin in which a double bond is placed in a central portion of a main chain may be obtained by appropriately controlling reaction conditions of dehydration, if a catalyst having extremely high or low activity is used, an amount of the olefin in which the double bond is placed in the central portion of the main chain may be maximized by recycling all or some of the LIO obtained after dehydration in consideration of operation stability.

When an estolide compound is prepared using the LIO prepared by the method as set forth above, there is a merit in that fatty acids excluding oleic acid do not remain. Of course, in other embodiments, a commercially available LIO may be used instead of the biomass-derived LIO.

Figure 5:
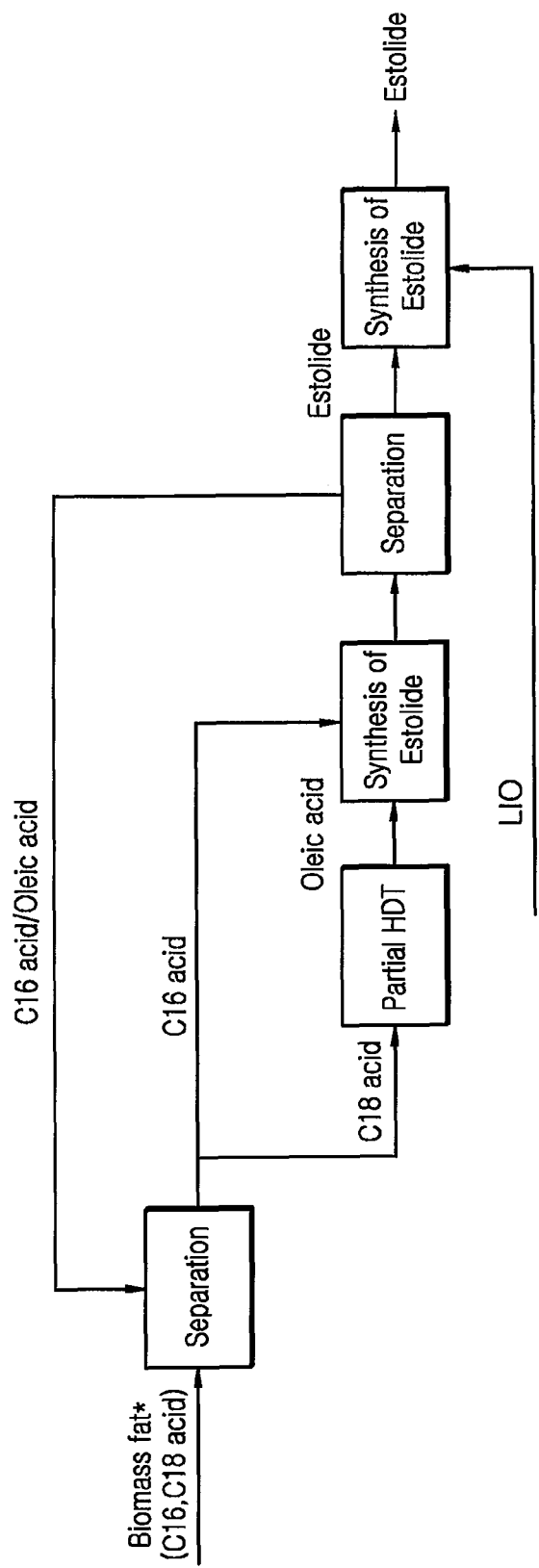
FIG. 5 is a process flowchart schematically showing a method for preparing an estolide compound according to another embodiment of the present invention.
Figure 6:
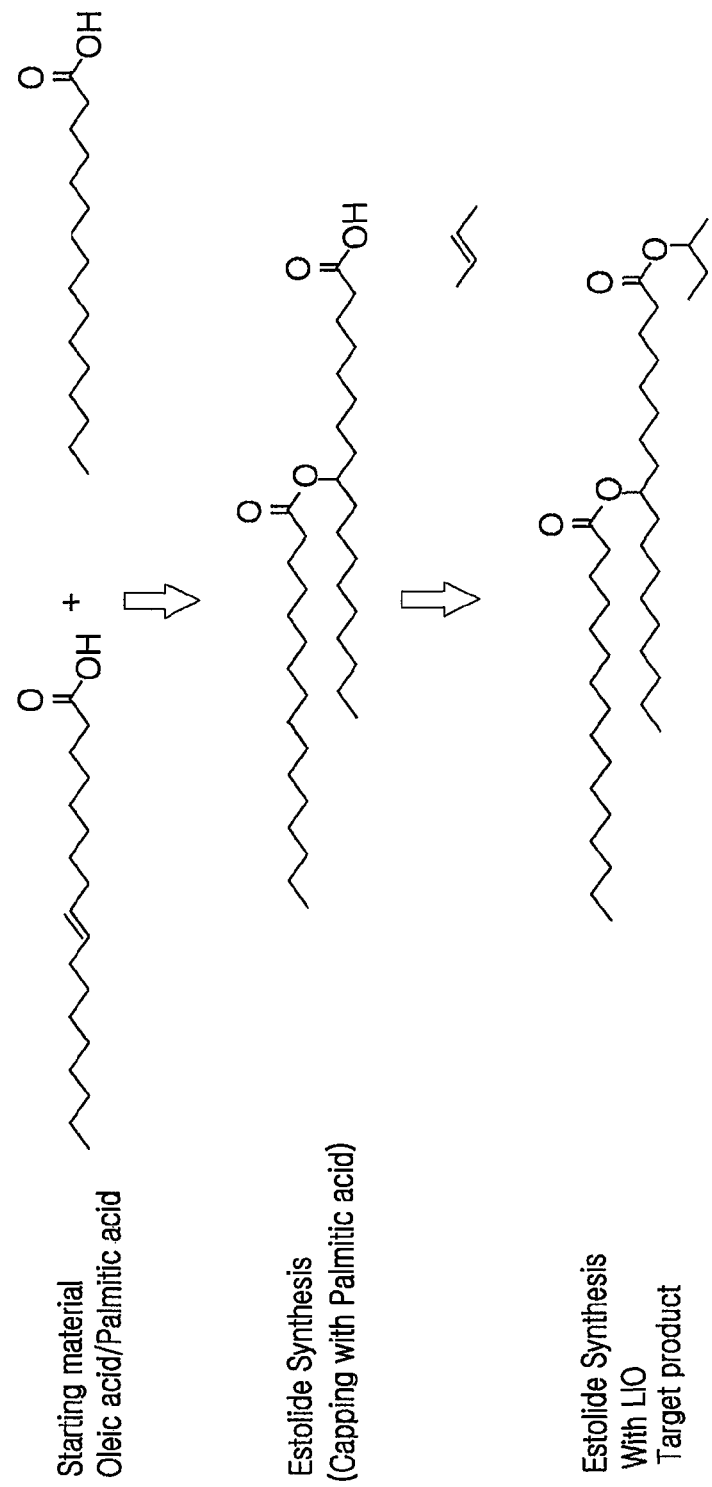
FIG. 6 shows a reaction mechanism of an estolide compound according to another embodiment of the present invention.
Figure 7:
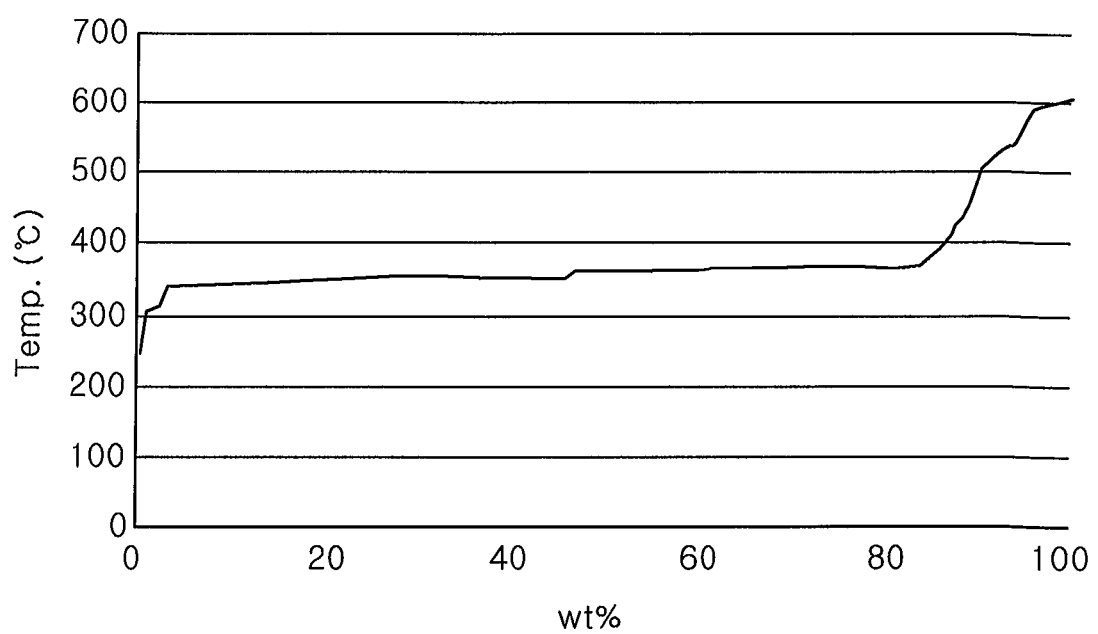
FIG. 7 is a graph depicting an analysis result (SimDist) of a PFAD specimen of Example.

FIG. 5 shows a process flowchart for preparing an estolide compound using a commercially available low-priced LIO according to another embodiment of the invention, and FIG. 6 shows a reaction mechanism of an estolide compound according to another embodiment of the present invention. Although there is an advantage in that properties of a prepared estolide compound can be controlled depending on a chemical structure of the commercially available LIO, process efficiency and economic feasibility can be further improved in that the remaining fatty acids excluding oleic acid out of the biomass-derived fatty acids are converted into LIO and used.

Operation S40 of performing partial hydrogenation of the C18 unsaturated fatty acid corresponds to increasing an amount of oleic acid by converting linoleic acid (C18:2), linolenic acid (C18:3) or the like of the biomass fat into oleic acid (C18:1). The $C_{18}$ unsaturated fatty acid may include about 90% or more of oleic acid through partial hydrogenation.

A catalyst used in partial hydrogenation is a supported catalyst in which NiMo, CoMo, or Mo is supported on a water resistant carrier.

Partial hydrogenation is performed under conditions of a temperature of about 160° C. to about 180° C. and a pressure of about 20 bar to about 40 bar rather than under conditions of a high temperature of 200° C. or more and a high pressure of 40 bar or more, which correspond to typical conditions for hydrogenation. If reaction is performed at a high temperature of 180° C. or more and a high pressure of 40 bar or more, the $C_{18}$ unsaturated fatty acid can be converted into stearic acid (C18:0) since all unsaturated double bonds are completely removed, or in severer cases, there can occur side reaction in which $C_{15}$ or $C_{17}$ linear paraffin is created due to decarboxylation.

For this reason, in order to control the reaction such that only one unsaturated double bond is present by partial saturation of olefins of the biomass fat, which have two or more unsaturated double bonds, the reaction is performed under the limited conditions as set forth above. Even though only some of the olefins having two or more unsaturated double bonds are converted into the olefins having one unsaturated double bond under the limited conditions as set forth above, since all of the olefins having two or more unsaturated double bonds are subjected to partial saturation by recycling, suppression of side reaction is a more important issue than reaction yield.

In addition, the conditions as set forth above differ from typical conditions for hydrogenation results in terms of characteristics of biomass. Biomass includes an extremely high amount of oxygen as compared with crude oil. When oxygen is removed through hydrogenation, oxygen is removed in the form of $H_2O$ through reaction with hydrogen and thus causes an active metal and a carrier of the catalyst to dissolve, thereby causing a problem of serious catalyst deactivation. Therefore, when biomass is subjected to hydrogenation, catalyst deactivation due to water created as a by-product can be extremely serious.

According to the present invention, a water resistant carrier, such as $ZrO_2$, $TiO_2$ and the like, is used, whereby the problem of catalyst deactivation due to such catalyst leaching can be overcome.

Operation S50 of synthesizing an estolide polymer through cross metathesis of the oleic acid may allow synthesis of an estolide polymer by forming an estolide bond through cross metathesis of the oleic acid which is present in the $C_{18}$ unsaturated fatty acid separated in operation S20 or is converted by partial hydrogenation in operation S40.

Cross metathesis may derive the estolide bond of the oleic acid by reacting the oleic acid with high-purity sulfuric acid, perchloric acid or the like in a batch reactor.

It is desirable that the sulfuric acid have a high purity of about 90% or more. If the sulfuric acid has low purity, since there is a drawback of significant reduction in reaction activity, attention should be paid to the purity of sulfuric acid.

Estolide bonding may be performed at a reaction temperature of 25° C. to 80° C. and at a reaction pressure of 0.1 bar to 10 bar.

Next, operation S60 of capping the $C_{16}$ saturated fatty acid secured in operation S20 onto the estolide polymer obtained in operation S50 is performed.

Capping the $C_{16}$ saturated fatty acid may be performed by introducing the estolide polymer secured in operation S50 and the $C_{16}$ saturated fatty acid secured in operation S20 in a weight ratio of 1:0.1 to 1:20 into a reactor, followed by reaction with high-purity sulfuric acid, perchloric acid or the like.

Capping the C16 saturated fatty acid may be performed at a reaction temperature of 25° C. to 80° C. and at a reaction pressure of 0.1 bar to 10 bar.

Next, the $C_{16}$ saturated fatty acid-capped estolide polymer secured in operation S60 may be prepared into a finally desired estolide compound through operation S70 of reacting the estolide polymer with the LIO prepared in operation S30.

Through operation S70, a fatty acid group placed at a terminal of the estolide polymer is converted into an ester group by reaction with the LIO, thereby stabilizing a chemical structure.

The estolide polymer secured in operation S60 and the LIO prepared in operation S30 are introduced in a weight ratio of 1:0.1 to 1:20 into the reactor, followed by reaction with high-purity sulfuric acid, perchloric acid or the like.

The reaction of the estolide polymer with the LIO may be performed at a reaction temperature of 25° C. to 80° C. and at a reaction pressure of 0.1 bar to 10 bar.

Estolide Compound

An estolide compound, which is prepared by the method as set forth above, may be represented by Formula 2.

[Formula 2]

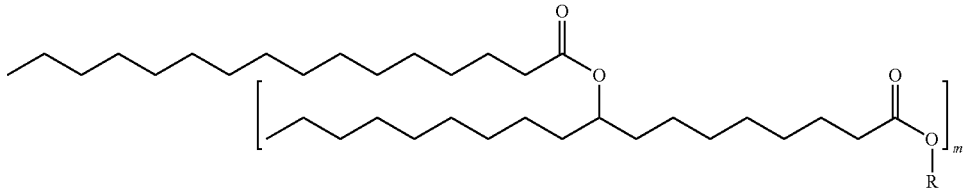

In Formula 2, m may be an integer of 1 to 6.

In Formula 2, the substituent R may be a $C_{2n}$ or $C_{2n+1}$ alkyl group, and n may be an integer from 2 to 12.

In Formula 2, the substituent R may be a $C_{2n}$ or $C_{2n+1}$ alkyl group; n may be an integer from 2 to 12; carbon placed at $C_{n-x}$ to $C_{n+x}$ may be bonded to an ester group; and x may be an integer from 2 to 4.

In one embodiment, in Formula 2, n may be an integer from 6 to 10, and x may be an integer from 1 to 2.

In another embodiment, the estolide compound may be a compound represented by Formula 3.

[Formula 3]

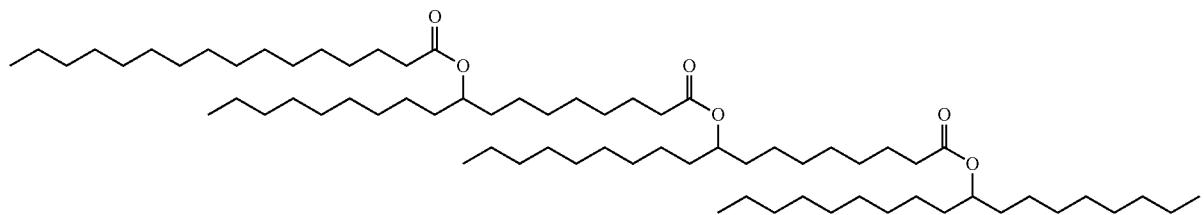

The estolide compounds represented by Formulae 2 and 3 have merits as an environmentally friendly lubricating oil, for example, high biodegradability and high viscosity index, and exhibits outstanding low-temperature stability and oxidative stability.

In addition, since the estolide compounds represented by Formulae 2 and 3 do not have an unsaturated double bond, there is no need for an HDF process. Further, since all structures in a molecule of the estolide compounds represented by Formulae 2 and 3 are formed by estolide bonds, the estolide compounds represented by Formulae 2 and 3 exhibit extremely high structural stability as compared with existing estolide compounds, and do not require an additional raw material such as alcohol and the like in a preparation process thereof.

According to one embodiment, an estolide compound has a pour point of about −45° C. to about −20° C. and a viscosity index of about 140 to about 180, and thus can exhibit excellent properties as a lubricating base oil.

Hereinafter, the present invention will be described in more detail with reference to some examples. However, it should be noted that these examples are provided for illustration only and are not to be construed in any way as limiting the present invention.

EXAMPLES

A. Separation of Fatty Acid 2 kg of a palm fatty acid distillate (PFAD) specimen was separated into fatty acids at each of reaction temperatures using a TBP cutting apparatus. From analysis results (SimDist) of the PFAD specimen shown in FIG. 3, it could be confirmed that the PFAD specimen included components present in amounts as listed in Table 1. The PFAD specimen was cut based on the reaction temperatures, that is, 300° C., 355° C. and 380° C., thereby obtaining fatty acids in amounts as listed in Table 2, respectively.

TABLE 1

| Fatty acid | Amount of component of PFAD (wt %) |
| --- | --- |
| Myristic acid (C14:0) | 3 |
| Palmitic acid (C16:0) | 43 |
| Oleic acid (C18:1), Linoleic acid (C18:2), Linolenic acid (C18:3) | 38 |
| Mono-, di-glyceride | 16 |
| Total | 100 |

TABLE 2

| Fatty acid | Boiling point (b.p.) | Amount of each fatty acid separated and obtained (g) |
| --- | --- | --- |
| Myristic acid (C14:0) | 300° C. or less | 56 |
| Palmitic acid (C16:0) | 300° C.~355° C. | 881 |
| Oleic acid (C18:1), Linoleic acid (C18:2), Linolenic acid (C18:3) | 355° C.~380° C. | 742 |
| Mono-, di-glyceride | 380° C. or more | 289 |
| Total | — | 1968 |

B. Preparation of Linear Internal Olefin (LIO)

In a 4 L autoclave reactor, 440.0 g of a $C_{16}$ saturated fatty acid (palmitic acid) secured in operation A, 20.4 g of anhydrous iron chloride ($FeCl_2$), 168 g of a triphenylphosphine and 163.2 g of acetic anhydride were introduced in order, followed by mixing. The reactor was purged with nitrogen ($N_2$) twice, followed by filling nitrogen to a pressure of 20 bar, thereby maintaining total reaction pressure at 20 bar. Next, the reactor was heated to 240° C., left for 10 minutes, and then shut down.

A recovered catalyst and a reaction product were filtered to separate the catalyst and the reaction product. The catalyst was stored separately for reuse, and the filtered reaction product was mixed with 2 L of deionized water (DI-water), and left for 24 hours while stirring the mixture. Next, the reaction product was separated from deionized water using a separatory funnel, followed by filtration of the remaining reaction product again through Celite. n-Heptane contained in the filtered reaction product was selectively separated using a vacuum fractional distillation apparatus (Spaltrohr HMS 300C, Fischer technology Co., Ltd.), thereby obtaining a final reaction product. The obtained reaction product was subjected to SimDist analysis, thereby measuring conversion rate. In addition, the obtained reaction product was subjected to GC-MS analysis, thereby confirming selectivity of an alpha-olefin out of olefin products and whether other side reaction occurred. Results are shown in Table 3.

TABLE 3

| Reaction temperature (° C.) | Total yield (%) | Total product weight (g) | Weight of $C_{15}$ olefin (g) |
| --- | --- | --- | --- |
| 240 | 80.3 | 355.9 | 351.0 |

From results of GC-MS analysis, it could be seen that a $C_{15}$ olefin was selectively created, only trace impurities remained, and almost no side reaction occurred. It was confirmed that there was almost no alpha-olefin in the olefins and most of the olefins were linear internal olefin. It was confirmed that the obtained $C_{15}$ olefin had a boiling point (b.p.) of about 270° C., and the $C_{15}$ LIO was secured by selectively separating oil having a boiling point (b.p.) of about 260° C. to about 275° C. from the obtained liquid product using a fractional distillation apparatus (Spaltrohr HMS 300C, Fischer technology Co., Ltd.).

C. Partial Hydrogenation for Improvement in Oleic Acid Yield 742 g of $C_{18}$ fatty acids (C18:1, C18:2, C18:3) obtained in separation of the fatty acids was subjected to partial hydrogenation in the presence of a $NiMo/ZrO_2$ catalyst, thereby converting linoleic acid (C18:2) and linolenic acid (C18:3) into oleic acid (C18:1).

From results of GC-MS analysis, it could be confirmed that linoleic acid and linolenic acid were converted into oleic acid with high selectivity, as shown in Table 4.

TABLE 4

| Fatty acid | Change in amount before and after partial hydrogenation (wt %) | |
|---|---|---|
| | Before | After |
| Oleic acid (C18:1) | 80.3 | 93.9 |
| Linoleic acid (C18:2) | 17.9 | 5.9 |
| Linolenic acid (C18:3) | 1.8 | 0.2 |

After partial hydrogenation, products in Table 3 were introduced into a 500 cc flask, followed by fractional distillation by connecting the flask to a fractional distillation apparatus (Spaltrohr HMS 300C, Fischer technology Co., Ltd.), thereby finally obtaining 682 g of oleic acid.

D. Estolide Bonding of Oleic Acid 341 g out of 682 g of the oleic acid obtained in operation C and 8.5 g of 70% purity perchloric acid were introduced into a 500 cc flask, which in turn was connected to a fractional distillation apparatus (Spaltrohr HMS 300C, Fischer technology Co., Ltd.). Next, the fractional distillation apparatus was heated to 60° C., followed by reducing the pressure of the fractional distillation apparatus to 10 torr, and then maintained for 24 hours while slowly stirring the components. The resulting material was introduced into a 2 L beaker, followed by quenching with a mixed solution of KOH/ethanol/DI-water (3.4 g/100 cc/900 cc) while stirring the resulting material. After confirming by pH measurement that remaining acid was not present in the mixed solution, the mixed solution was left until the temperature of the mixed solution decreased. Next, the mixed solution was introduced into a separatory funnel and settled, followed by selectively removing a water layer after the water layer and an organic layer were separated. The separated organic layer was introduced again into the fractional distillation apparatus (Spaltrohr HMS 300C, Fischer technology Co., Ltd.), and cut at 385° C., thereby removing the unreacted material. 49 g of the unreacted material was separated, and 274 g of an estolide polymer was secured.

E. Capping Palmitic Acid onto Estolide Polymer 274 g of the estolide polymer obtained in operation D, 124 g of the palmitic acid separated in operation A and 6.8 g of 70% purity perchloric acid were introduced into a 500 cc flask, which in turn was connected to a fractional distillation apparatus (Spaltrohr HMS 300 C, Fischer technology Co., Ltd.). Next, the fractional distillation apparatus was heated to 60° C., followed by reducing the pressure of the fractional distillation apparatus to 10 torr through vacuum treatment, and then maintained for 12 hours while slowly stirring the components. The resulting material was introduced into a 2 L beaker, followed by quenching with a mixed solution of KOH/ethanol/DI-water (2.8 g/100 cc/900 cc) while stirring the resulting material. After confirming by pH measurement that remaining acid was not present in the mixed solution, the mixed solution was left until the temperature of the mixed solution decreased. Next, the mixed solution was introduced into a separatory funnel and settled, followed by selectively removing a water layer after the water layer and an organic layer were separated. The separated organic layer was introduced again into the fractional distillation apparatus (Spaltrohr HMS 300C, Fischer technology Co., Ltd.), and cut at 550° C., thereby removing unreacted material. 163 g of the unreacted material was separated, and 210 g of the palmitic acid-capped estolide polymer was obtained.

F. Reacting Estolide Polymer with LIO 210 g of the palmitic acid-capped estolide polymer obtained in operation E, 67 g of the $C_{15}$ LIO secured in operation B and 6.0 g of 70% purity perchloric acid were introduced into a 500 cc flask, which in turn was connected to a fractional distillation apparatus (Spaltrohr HMS 300C, Fischer technology Co., Ltd.). Next, the fractional distillation apparatus was heated to 60° C., followed by reducing the pressure of the fractional distillation apparatus to 10 torr through vacuum treatment, and then maintained for 12 hours while slowly stirring the components. The resulting material was introduced into a 2 L beaker, followed by quenching with a mixed solution of KOH/ethanol/DI-water (2.5 g/100 cc/900 cc) while stirring the resulting material. After confirming by pH measurement that remaining acid was not present in the mixed solution, the mixed solution was left until the temperature of the mixed solution decreased. Next, the mixed solution was introduced into a separatory funnel and settled, followed by selectively removing a water layer after the water layer and an organic layer were separated. The separated organic layer was introduced again into the fractional distillation apparatus (Spaltrohr HMS 300C, Fischer technology Co., Ltd.), and cut at 650° C., thereby removing the unreacted material. 77 g of the unreacted material was separated, and 185 g of an estolide compound was finally prepared.

The estolide compound was evaluated as to properties as a lubricating oil, and results are shown in Table 5.

TABLE 5

| Viscosity (40° C.) | Viscosity (100° C.) | Viscosity index (VI) | Pour point (PP) | Iodine value |
|---|---|---|---|---|
| 19.3 Cst | 125.8 Cst | 174 | −43° C. | 0.07 cg/g |

As shown in Table 5, the estolide compound prepared in Example exhibited high lubricating-oil properties in terms of VI and PP, and did not have remaining unsaturated double bonds due to the significantly low iodine value thereof.

Although the present invention has been described with reference to some embodiments in conjunction with the accompanying drawings, it should be understood that the present invention is not limited to the foregoing embodiments and may be embodied in different ways, and that various modifications, changes, alterations, and equivalent embodiments can be made by those skilled in the art without departing from the spirit and scope of the invention. Therefore, it should be understood that the foregoing embodiments are provided for illustrative purposes only and are not to be construed in any way as limiting the present invention.

Since the estolide compound according to the present invention does not have unsaturated bonds, the estolide compound exhibits excellent low-temperature stability and oxidative stability. In addition, the method according to the present invention allows remaining fatty acids excluding oleic acid out of biomass-derived fatty acids to be converted into a linear internal olefin (LIO) and used, can minimize dependency on oleic acid upon preparation of an estolide compound by increasing the amount of oleic acid, and can provide excellent process efficiency and economic feasibility by eliminating use of alcohols.

What is claimed is:

1. A method for preparing an estolide compound, comprising:
converting biomass fat into a fatty acid;
separating the fatty acid into a $C_{16}$ saturated fatty acid and a $C_{18}$ unsaturated fatty acid;
preparing a linear internal olefin (LIO);
increasing an amount of oleic acid through partial hydrogenation of the $C_{18}$ unsaturated fatty acid;
synthesizing an estolide polymer through cross metathesis of the oleic acid;
capping the $C_{16}$ saturated fatty acid onto the estolide polymer; and
reacting the estolide polymer with the linear internal olefin.

2. The method according to claim 1, wherein the $C_{16}$ saturated fatty acid is palmitic acid, and the $C_{18}$ unsaturated fatty acid comprises oleic acid, linoleic acid and linolenic acid.

3. The method according to claim 1, wherein the linear internal olefin is prepared through decarbonylation of some of the biomass-derived fatty acid.

4. The method according to claim 3, wherein decarbonylation is performed at a reaction temperature of about 180° C. to about 250° C. for about 1 minute to about 600 minutes.

5. The method according to claim 1, wherein the linear internal olefin is prepared using partial hydrogenation for converting the biomass-derived fatty acid into a fatty alcohol and dehydration.

6. The method according to claim 5, wherein partial hydrogenation is performed at a reaction temperature of about 120° C. to about 500° C. and at a reaction pressure of about 1 bar to about 30 bar in terms of $H_2$, and dehydration is performed at a reaction temperature of 250° C. to 500° C.

7. The method according to claim 5, wherein dehydration is performed in the presence of at least one metal oxide catalyst selected from the group consisting of alumina, silica-alumina, zirconia, titania, iron oxide, vanadium oxide, zeolite, and alumina-supported mesoporous silica.

8. The method according to claim 1, wherein the linear internal olefin is a $C_{15}$ linear internal olefin prepared by converting some of the $C_{16}$ saturated fatty acid.

9. The method according to claim 1, wherein increasing the amount of oleic acid through partial hydrogenation of the $C_{18}$ unsaturated fatty acid is performed at a reaction temperature of about 160° C. to about 180° C. and at a reaction pressure of about 20 bar to about 40 bar in the presence of a supported catalyst in which NiMo, CoMo or Mo is supported on a water resistant carrier.

10. The method according to claim 9, wherein the water resistant carrier is $ZrO_2$ or $TiO_2$.

11. The method according to claim 1, wherein the $C_{18}$ unsaturated fatty acid comprises 90% or more of oleic acid through partial hydrogenation.

12. The method according to claim 1, wherein, in synthesizing an estolide polymer through cross metathesis of the oleic acid, cross metathesis is performed at a reaction temperature of about 25° C. to about 80° C. and at a reaction pressure of about 0.1 bar to about 10 bar.

13. The method according to claim 1, wherein, in capping the $C_{16}$ saturated fatty acid onto the estolide polymer, the estolide polymer and the $C_{16}$ saturated fatty acid react in a weight ratio of about 1:0.1 to about 1:20 at a reaction temperature of about 25° C. to about 80° C. and at a reaction pressure of about 0.1 bar to about 10 bar.

14. The method according to claim 1, wherein, in reacting the estolide polymer with the linear internal olefin (LIO), the estolide polymer and the LIO react in a weight ratio of about 1:0.1 to about 1:20 at a reaction temperature of about 25° C. to about 80° C. and at a reaction pressure of about 0.1 bar to about 10 bar.

* * * * *